United States Patent [19]

Takenaka

[11] Patent Number: 5,114,081

[45] Date of Patent: May 19, 1992

[54] SYSTEM FOR MECHANICALLY AND BIOLOGICALLY DECOMPOSING GARBAGE

[75] Inventor: Shintaro Takenaka, Fukuyama, Japan

[73] Assignees: Mitsui Home Co., Ltd., Tokyo; Shinyou Sangyo Co., Ltd., Hiroshima, both of Japan

[21] Appl. No.: 700,802

[22] Filed: May 16, 1991

[30] Foreign Application Priority Data

Nov. 14, 1990 [JP] Japan .................... 2-308378

[51] Int. Cl.⁵ ............................. B02C 21/00
[52] U.S. Cl. ........................ 241/79; 210/173; 210/415; 241/1; 241/301; 422/229; 422/273; 422/275
[58] Field of Search ............... 241/1, 79, 100.5, 301; 210/173, 415; 422/229, 271, 273, 275, 276; 435/287; 71/10, 11, 14

[56] References Cited

U.S. PATENT DOCUMENTS

| | | | |
|---|---|---|---|
| 2,212,062 | 8/1940 | Dueer et al. | 71/14 |
| 3,823,879 | 7/1974 | Johnson | 241/100.5 X |
| 4,326,874 | 4/1982 | Bürklin | 71/14 X |
| 5,009,795 | 4/1991 | Eichler | 210/415 X |

*Primary Examiner*—Douglas D. Watts
*Attorney, Agent, or Firm*—Cushman, Darby & Cushman

[57] ABSTRACT

A system for mechanically and biologically decomposing a garbage discharged from a house, a restaurant or the like at high operational efficiency is disclosed. The system includes a disposer for disintegrating the garbage into a large number of pieces, a solid/liquid separator for separating water from the disintegrated garbage and a garbage decomposing vessel for biologically dissolving the solid disintegrated garbage from which water has been substantially separated in the solid/liquid separator. To promote biological decomposition of the solid disintegrated garbage in the garbage decomposing vessel, pulverized wood is normally used instead of soil as a raw material for forming a decomposing bacillus growing bed in the garbage decomposing vessel. Prior to practical use, the pulverized wood is thermally processed.

4 Claims, 5 Drawing Sheets

SYSTEM FOR MECHANICALLY AND BIOLOGICALLY DECOMPOSING GARBAGE

BACKGROUND OF THE INVENTION

1. Field of the Invention

The present invention relates generally to a system for mechanically and biologically decomposing garbage. More particularly, the present invention relates to a system for mechanically and biologically decomposing garbage such as kitchen waste material from a house, a restaurant or the like and industrial waste material from a foodstuff industry, an animal feed industry or the like.

2. Field of the Invention

Among various methods for disposing a foodstuff waste material, a widely employed method is to bury the waste material in the ground and another widely employed method is to dispose of the waste material by incinerating it. In this country, generally, garbage discharged from each house is disposed of by self-governing body and a foodstuff waste material from a foodstuff industry is disposed of as industrial waste material by an operator specializing in dealing with waste materials. However, the current status is that most of operators specializing in dealing with industrial waste materials utilize disposing facilities which are built and owned by the self-governing body. This means that they are merely a transporter, who transports the industrial waste materials to a certain burying location or an incinerator owned by the selfgoverning body. In the past, pig breeders collected foodstuff waste materials as fodder. In recent years, things changed due to not only a shortage in manpower but also a low price of pig meat in a meat market, causing the pig breeder to employ an artificial composite fodder for breeding pigs. This leads to the result that all the foodstuff waste materials are currently disposed by employing the burying method or the incinerating method.

As described above, the method of disposing foodstuff waste materials is divided into two types, i.e., the burying method and the incinerating method. However, each of the methods becomes a source of significant industrial public pollution in modern society.

(1) In practice, the burying method is accomplished by burying waste materials in a burying site peripheral to a sea or a burying site in a mountain or valley. Alternatively, the waste materials are buried in a location sufficiently deep below the ground surface. However, each of the aforementioned cases leads to a destruction of the natural environment. In view of the current status wherein worldwide attention has been paid to protection of the natural environmental from destruction, it is believed that a measure to be taken against pollution of a sea, river and others should seriously be considered and discussed as a significant problem to be solved in the near future.

The most significant problems inherent to the burying method are that noxious insects are born and grown in the burying site and unpleasant odor is generated from the burying site, whereby people living in the proximity of the burying site unavoidably suffer from the noxious insects and the unpleasant odor. It is believed that this problem is derived from a limited narrow area or space which is generally available in this country for practicing the burying method as well as a limited quantity of waste materials to be buried per unit area.

(2) On the other hand, the most significant problems inherent to the incinerating method are that an incinerator is manufactured at a expensive cost and it becomes increasingly difficult to obtain a previous agreement and approval from people living in the proximity of an incinerator to be installed.

Garbage to be disposed by employing the incinerating method functions like water. In other words, disposition of the garbage is similar to vaporizing water by burning heavy oil. Accordingly, burying of the garbage with oil leads to a significant loss of energy which in turn causes a loss for human beings. In addition, it becomes increasingly unacceptable from the viewpoint of protection of the natural environment and the human beings from destruction or injury to employ the burying method for disposing of garbage, since carbon dioxide gas is generated during an incinerating operation and various noxious matters are simultaneously scattered in the air.

(3) Next, with respect to disposition of a garbage discharged from each house, self-governing bodies have taken positive actions since about ten years ago for allowing the garbage from each house to be disposed by each house itself as far as possible because of a limited capacity of disposing of the garbage in an incinerator owned by each self-governing body.

Specifically, each self-governing body has recommended employment of a bottomless container molded of plastic resin for the purpose of biologically decomposing kitchen garbage naturally. The container is practically used such that the garbage is put in the bottomless container mounted directly on the ground and a cover is then placed on the container so that the garbage is biologically decomposed in the presence of soil as time elapses. However, it has been found that the conventional method which has been positively recommended by self-governing bodies until now to use the bottomless container in the above-described manner has the following drawbacks.

(1) To practice the method, a certain quantity of soil is absolutely necessary.

(2) Unpleasant odor is increasingly generated from the container day by day.

(3) Noxious worms and insects such as grubs, flies or the like are born and grown in the container.

(4) Although kitchen garbage can biologically be decomposed in the container naturally, it is unavoidable that so-called overflow occurs as a certain quantity of garbage is put in the container day by day.

(5) The container is employed based on a fundamental condition that the finally disposed material is utilized as a fertilizer. If no farm is available for an user, the resultant material can not practically be used as a fertilizer irrespective of some available quantity of soil for biological decomposition of the garbage.

(6) To provide the container for each user at an inexpensive cost, it is molded of plastic resin while having a very thin wall. For this reason, the container is readily damaged or broken by a small magnitude of force imparted thereto from the outside.

(7) The container which has been employed at present is molded of plastic resin having less resistance to the elements. Thus, the container is naturally damaged or broken as time elapses.

(8) Dogs or cats often bring the decomposing garbage away from the container to the outside. This induces a so-called scattering pollution.

At present, the method recommended by self-governing bodies is mostly employed by individual houses located in the suburbs. Therefore, each self-governing body does not suffer directly from problems associated with decomposition of kitchen garbage but each house in a city, town or the like suffers from these problems.

To obviate the above problems, it has been proposed to use an apparatus for storing a garbage in a refrigerated state or an electronic range type incinerator for the purpose of disposing of garbage. However, it is obvious that the foregoing proposal is not a complete resolution of the problems.

SUMMARY OF THE INVENTION

The present invention has been made with the foregoing background in mind.

An object of the present invention is to provide a system for mechanically and biologically decomposing garbage in a highly sanitary manner at a high operational efficiency.

Another object of the present invention is to provide a system for mechanically and biologically decomposing garbage wherein all problems from which self-governing bodies, houses and industries are currently suffering can completely be obviated.

To accomplish the above objectives, the present invention provides a system for mechanically and biologically decomposing garbage, wherein the system comprises a disposer for disintegrating the garbage, a solid/liquid separator arranged downstream of the disposer to receive the garbage which has been disintegrated by the disposer, the solid/liquid separator serving to separate water from the disintegrated garbage, and garbage decomposing vessel arranged downstream of the solid/liquid separator to receive the solid disintegrated garbage from which water has been substantially separated in the solid/liquid separator, the garbage decomposing vessel serving to biologically dissolve the solid disintegrated garbage.

According to the present invention, as the garbage is introduced into the interior of the disposer, it is disintegrated into a large number of pieces by the disposer and the disintegrated garbage is then conveyed to the solid/liquid separator in which water is separated from the disintegrated garbage.

As water is separated from the disintegrating garbage in the solid/liquid separator, it is drained to a storing tank via an outlet port and the dewatered disintegrated garbage only is forcibly introduced into the interior of the garbage decomposing vessel by rotation of a the spiral conveying blade.

The dewatered disintegrated garbage is effectively stirred in the garbage decomposing bacillus growing bed in a presence of garbage decomposing bacilli by rotation as well as a turning movement of the spiral stirring blade, whereby the dewatered disintegrated garbage is biologically decomposed in the garbage decomposing vessel.

Next, biological decomposition of the garbage will be described below in more detail.

As is well known, kitchen garbage is mainly composed of various kinds of organic materials. All the organic materials are normally produced by nature with the exception of additives to be added to them. Accordingly, the garbage derived from these organic materials has been basically returned to nature in accordance with nature's rule. As far as nature's rule is concerned, the garbage is biologically decomposed in the presence of garbage decomposing bacilli such as soil bacilli, aqueous bacilli, optical synthetic bacilli or the like. However, biological decomposition of the organic materials in accordance with nature's rule has many drawbacks. Specifically, the biological decomposition of the garbage takes long time, various kinds of noxious insects are born and grown, disease bacilli are likewise born and grown and bad-smelling odor is unavoidably generated during a process of biological decomposition of the organic materials. It should be added that nature has a limit with respect to biological decomposition of the organic materials in the ground and that the extent of biological decomposition of the organic materials varies largely depending on imbalance among bacilli in the ground due to the presence of various kinds of soils as well as an intensity of penetration of oxygen in the air into the soil. It is natural that temperature and moisture have a significant effect on the results derived from the biological decomposition of the garbage.

It is well known that bacilli living in the ground below the ground surface by a depth of one meter or more are largely different from bacilli living on the ground surface with respect to kind and quantity and that the degree of biological decomposition of the organic materials varies on a case by case basis.

Provided that garbage composed of various kinds of organic materials is buried in the ground for the purpose of biological decomposition thereof in the present of bacilli, an obvious fact is that there are living many kinds of other bacilli whose presence has not been known and confirmed by experts and scholars in the art of biological decomposition because a repeated process of birth, growth and death of these bacilli in the ground has been not completely known by anybody. For example, a bacillus serving to eat disease bacilli, a bacillus serving to eat other bacilli and a bacillus serving as a source for self-growing of an organic material can typically be noted. The aforementioned nature's rule is applicable also to a human being's society and it has been heretofore required to sincerely conform with the nature's rule to establish a good harmonization with the human being's society. In view of the aforementioned current status, the present invention has succeeded in solving the above problems in proper consideration of weather conditions based on good harmonization with a pattern of daily living of the human beings.

Next, a plurality of means employed for carrying out the present invention will individually be described below in more detail.

(1) With respect to method of decomposing garbage in the water within a short period of time, an apparatus for carrying out this method is manufactured at an expensive cost. For this reason, the present invention is based on the same principle as the conventional principle of burying garbage in the ground in accordance with. To carry out the present invention, pulverized wood is employed instead of soil. Prior to practical use, the pulverized wood is thermally processed at a temperature of 130° C. for the purpose of removing various noxious substances in the pulverized wood and sterilizing the same. This step of previous processing is intended to promote growth of garbage decomposing bacilli, elevate the temperature of growing the garbage decomposing bacilli and to remove from the garbage decomposing vessel a lignin acid which is effective for preventing sprouts from growing. Consequently, the resultant products derived from the system of the present invention can be utilized as a fertilizer having improved safety.

(2) Generating of odor during natural decomposition of the garbage is attributable to various kinds of bad-smelling gases generated during natural decomposition of the garbage. According to the present invention, the problem concerning generation of the odor has been solved by using aerobic bacilli in the garbage decomposing vessel for biological decomposition to improve the capability of decomposition of the garbage and moreover employing very finely pulverized wood to form garbage decomposing bacillus growing bed having a excellent air permeability and porosity. Compressed air may be blown in the garbage decomposing vessel, as required.

In addition, to completely prevent a part of the solid disintegrated garbage from floating up on the upper surface of the garbage decomposing bacillus growing bed, arrangement is made such that the surface layer of the garbage decomposing bacillus growing bed having a certain height or thickness is kept in the non-stirring state in order to eliminate or minimize generation of unpleasant odor.

(3) It has been hitherto considered that it is practically impossible to prevent noxious worms and insects from being born and grown during a step of decomposition of organic materials. In other words, decomposition of the organic materials has been heretofore unavoidably accompanied by generation of specific unpleasant odor. However, according to the present invention, arrangement of the system as described in the preceding paragraph (2) has eliminated the problem concerning birth and growth of noxious insects and worms in the garbage decomposing vessel.

Therefore, no restriction is required as to the location where the system of the present invention is installed. The system may be installed on a veranda or a kitchen inlet. Alternatively, the system may be installed at a certain outdoor location.

(4) To promote decomposition of an organic garbage, the system of the present invention may be utilized such that the garbage is introduced into the interior of the system as it is left in the original state thereof. However, it is effective from the viewpoint of designing and constructing the system in smaller dimensions that the garbage is disintegrated into a large number of pieces by a disposer to enlarge an effective exposure surface area of the garbage. If garbage is introduced directly into the interior of the garbage decomposing vessel together with water required by the disposer, there arises a problem that a long time is taken until the garbage is completely decomposed, because the garbage is washed with water each time the garbage is introduced into the garbage decomposing vessel.

One of the significant features of the present invention is that the garbage which has been disintegrated by the disposer is conveyed to a solid/liquid separator in which water is separated from the disintegrated garbage and it is then drained to the outside. The dewatered disintegrated garbage is forcibly conveyed to the garbage decomposing vessel in which it is biologically decomposed until its original shape disappears within a certain period of time, e.g., one to two days. With such construction, since the garbage is decomposed so that a quantity of finally decomposed material is larger than a quantity of garbage to be decomposed, e.g., in a case where 1 Kg of kitchen garbage is daily discharged from a single house composed of five persons, it has been confirmed that the system of the present invention can satisfactorily be operated with a capacity of 40 to 60 liters.

(5) According to the present invention, garbage is biologically decomposed in accordance with nature while water is separated from the disintegrated garbage. In addition, pulverized wood is employed for forming garbage decomposing bacillus growing bed instead of soil after it is previously processed at an elevated temperature for removing various noxious matters therefrom. Thus, the resultant product derived from biological decomposition in the garbage decomposing vessel after a certain period of time elapses can be utilized as an organic fertilizer. This means that the system of the present invention matches well with the recent tendency for an agricultural process to be practiced using an organic fertilizer.

(6) The disposer is arranged by the sink of a kitchen in a house or the sink of a restaurant. As garbage is put in the disposer by an user, the disintegrated garbage is conveyed to the solid/liquid separator together with water so that the dewatered disintegrated garbage is forcibly introduced into the interior of the garbage decomposing vessel while the separated water is drained to the outside. The dewatered disintegrated garbage is stirred together with the pulverized wood and the garbage decomposing bacilli in the garbage decomposing vessel in operative association with the disposer. On completion of the stirring operation, the garbage decomposing vessel is automatically brought to an inoperative state. Therefore, a significant feature of the present invention consists in that no manpower is required at all.

Additionally, since the system of the present invention is constructed in possibly reduced dimensions with a small number of components while using materials each having excellent resistance to the elements, the system can practically used for a longer running period of time. Attention has been paid to selection of raw materials required for constituting the system such that employment of steel-based material is minimized and materials each having an excellent property with respect to resistance against oxidation, ultraviolet rays and mechanical stress are selectively used.

Other objects, features and advantages of the present invention will become apparent from the following description which has been made in conjunction with the accompanying drawings.

BRIEF DESCRIPTION OF THE DRAWINGS

The present invention is illustrated in the following drawings in which.

DESCRIPTION OF THE PREFERRED EMBODIMENTS

The present invention will be described in detail hereinafter with reference to the accompanying drawings which illustrates a system for mechanically and biologically decomposing garbage in accordance with preferred embodiments of the present invention.

Figure 1:
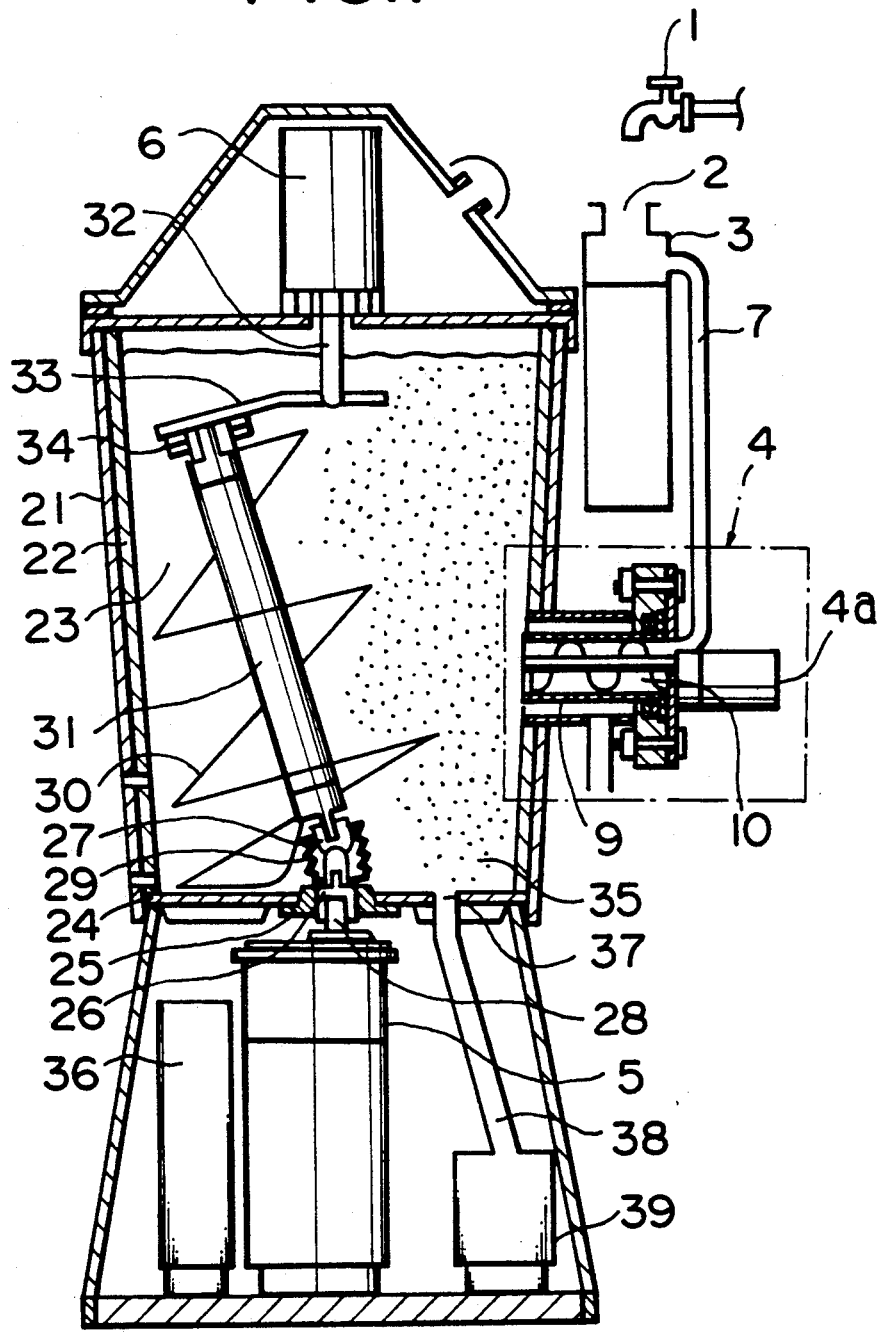
FIG. 1 is a vertical sectional view which schematically illustrates the whole structure of a system for mechanically and biologically decomposing garbage in accordance with an embodiment of the present invention.
Figure 2:
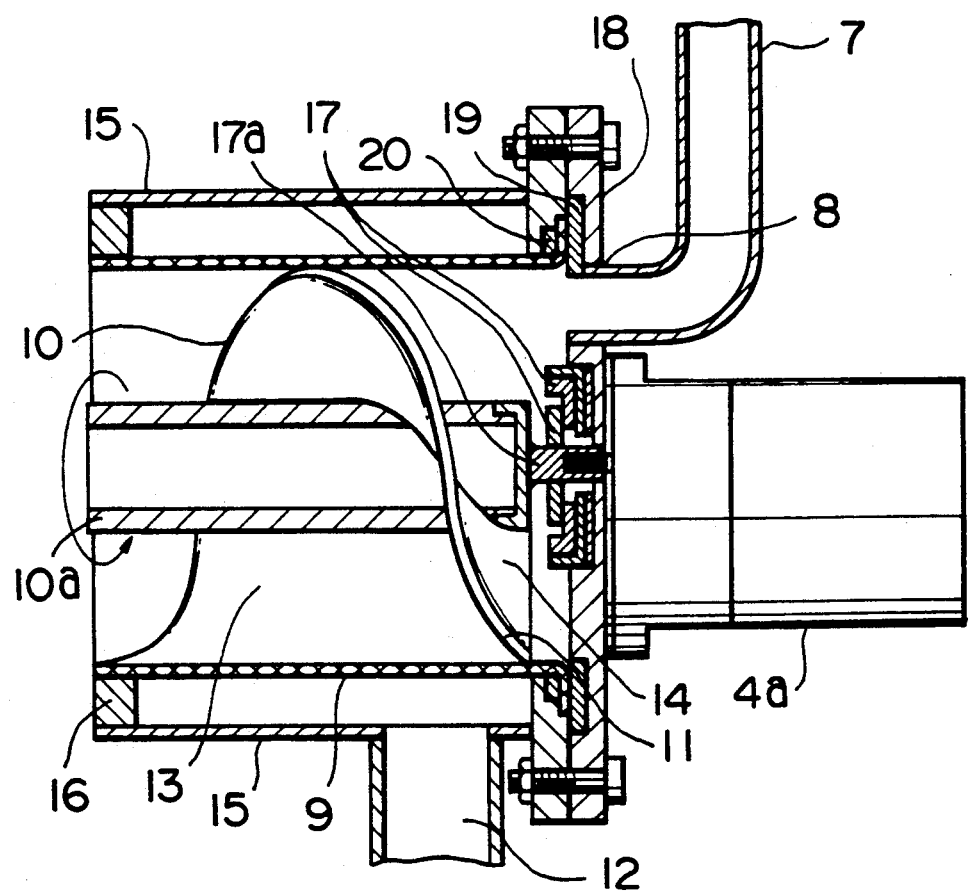
FIG. 2 is a fragmentary sectional view of the system in FIG. 1, particularly illustrating essential components constituting a solid/liquid separator.
Figure 3:
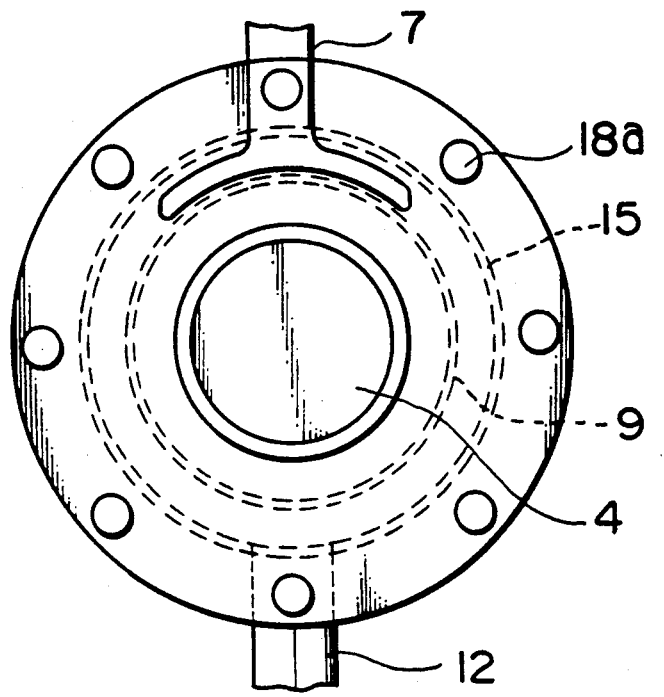
FIG. 3 is a side view of the system, particularly showing the solid/liquid separator as seen from the motor side of the solid/liquid separator.
Figure 4:
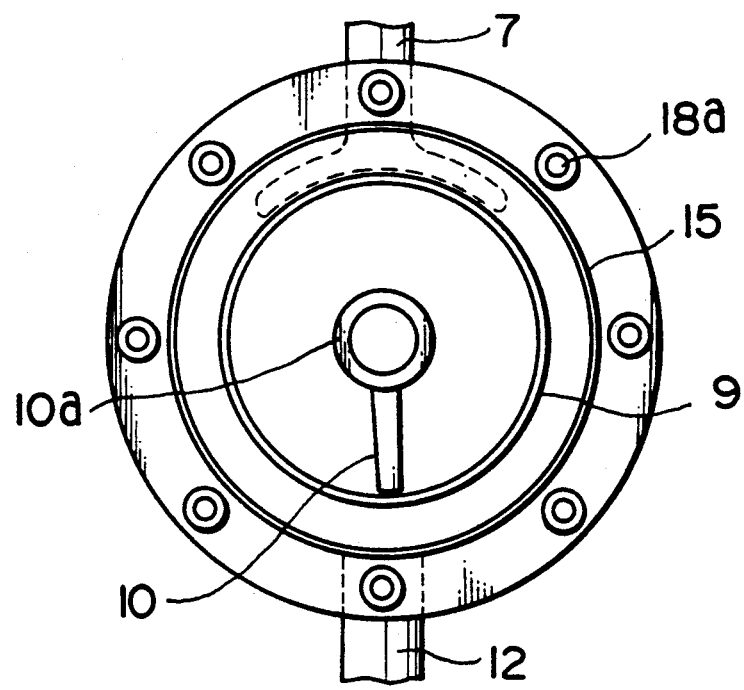
FIG. 4 is a side view of the system, particularly showing the solid/liquid separator as seen from the garbage discharging side of the solid/liquid separator.

As shown in FIG. 1 and FIG. 2, the garbage derived from a kitchen, a foodstuff processing shop or the like location is introduced into the interior of a disposer 3 via an inlet port 2 together with water delivered from a valve 1 as it is. When the disposer 3 is filled with the garbage to a certain extent, the disposer 3 is rotationally driven by a motor (not shown). At this time, a motor 4a for rotating a solid/liquid separator 4, a motor 5 for rotating a spiral stirring blade 30 and a motor 6 for turning the stirring blade are substantially simultaneously driven.

As the garbage is disintegrated in a large number of pieces, the disintegrated garbage is conveyed to the solid/liquid separator 4 together with water via a piping 7.

Next, the solid/liquid separator 4 will be described in more detail below with reference to FIG. 2.

The disintegrated garbage is introduced into the interior of a cylindrical solid/liquid separating screen 9 together with water. Since a spiral conveying blade 10 for conveying the garbage is rotated while the outer peripheral surface 11 of the spiral conveying blade 10 comes in close contact with the inner wall surface of the solid/liquid separating screen 9, a certain quantity of the garbage is temporarily accumulated together with water in the region in the vicinity of an inlet port 8. However, as the spiral conveying blade 10 is rotated, water falls down through a large number of holes on the solid/liquid separating screen 9 and is then drained to the outside via an outlet port 12.

Figure 5:
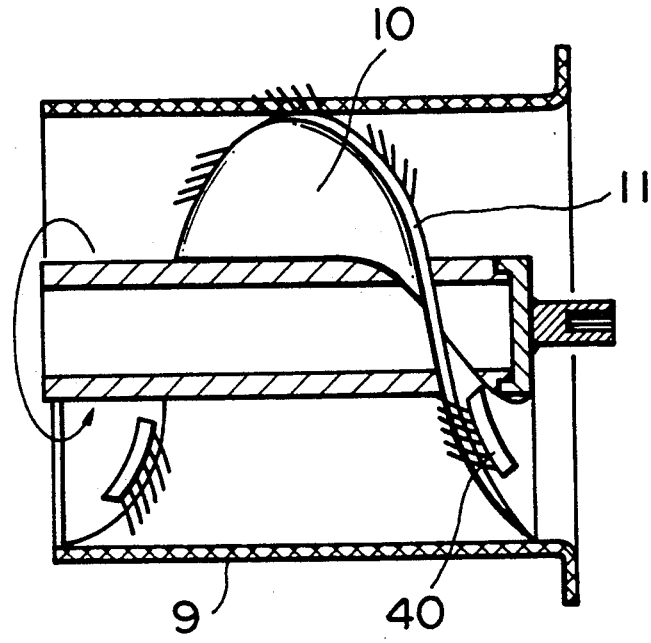
FIG. 5 is a fragmentary sectional view of the system in FIG. 1, particularly illustrating that a plurality of wire brushes are fixedly attached to a spiral conveying blade for the purpose of cleaning a solid/liquid separating screen.
Figure 6:
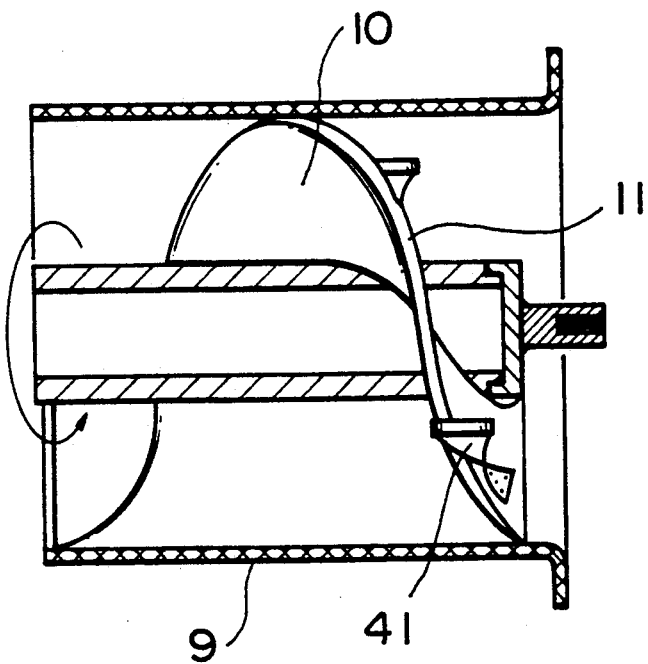
FIG. 6 is a fragmentary sectional view of the system similar to FIG. 5, particularly illustrating that a plurality of leaf springs are fixedly attached to the spiral conveying blade for the purpose of cleaning the solid/liquid separating screen.

There rarely arises a malfunction that the solid/liquid separating screen 9 is undesirably clogged with disintegrated garbage particles, since the outer peripheral surface 11 of the spiral conveying blade 10 normally comes in close contact with the inner wall surface of the solid/ liquid separating screen 9 and moreover the solid/liquid separating screen 9 is dimensioned to have a small thickness of 0.3 mm to 0.5 mm. However, in a special case where industrial waste materials are to be decomposed, there is a possibility that the solid/liquid separating screen 9 is clogged with waste material particles. To obviate this problem, a plurality of wire brushes 40 are fixedly attached to the rear surface 14 of the spiral conveying blade 10 to continuously clean the solid/liquid separating screen 9 as the spiral conveying blade 10 is rotated, as shown in FIG. 5. Alternatively, a plurality of leaf springs 41 may fixedly be attached to the rear surface 14 of the spiral conveying blade 10 for the same purpose, as shown in FIG. 6. It should be noted that arrangement of the wire brushes 40 or the leaf springs 41 in the above-described manner has been proposed based on a number of practical experiences. In fact, a proposal was made such that ball bearings or spring-loaded rods were mounted around the outer peripheral surface 11 of the spiral conveying blade 10 for the purpose of cleaning the solid/liquid separating screen 9 but it was found that the proposal was impractical because the spiral conveying blade 10 was rotated at a slow speed and thereby a cleaning operation was performed merely for a part of the contact region between the solid/liquid cleaning screen 9 and the spiral conveying blade 10. Thus, firm attachment of the cleaning brushes 40 or the leaf springs 41 to the rear surface 14 of the spiral conveying blade 10 has been proposed in order to obviate the foregoing problem inherent to the aforementioned prior proposal. It has been confirmed that firm arrangement of the cleaning brushes 40 or the leaf springs 41 assures that a rotary cleaning operation is performed with a wide width, causing a capability of solid/liquid separating to be improved substantially.

A water sealing ring 16 is fitted into the annular space between the solid/liquid separating screen 9 and an outer casing 15 in order to prevent the water separated in the annular space therebetween from the garbage through the holes on the solid/liquid separating screen 9 from entering garbage decomposing vessel 23 to be described later.

It should be added that a mechanical seal 17, a flange-shaped wall 18, a flange-shaped packing ring 19 and a packing ring 20 serving also as a bearing for a shaft portion 17a prevent an occurrence of water leakage. As is apparent from FIG. 1, the outer casing 15 is fixedly secured to an outer casing 15 of the garbage disposing vessel 23 at the substantially middle position as seen in the direction of a depth of the outer casing 15.

Figure 7:
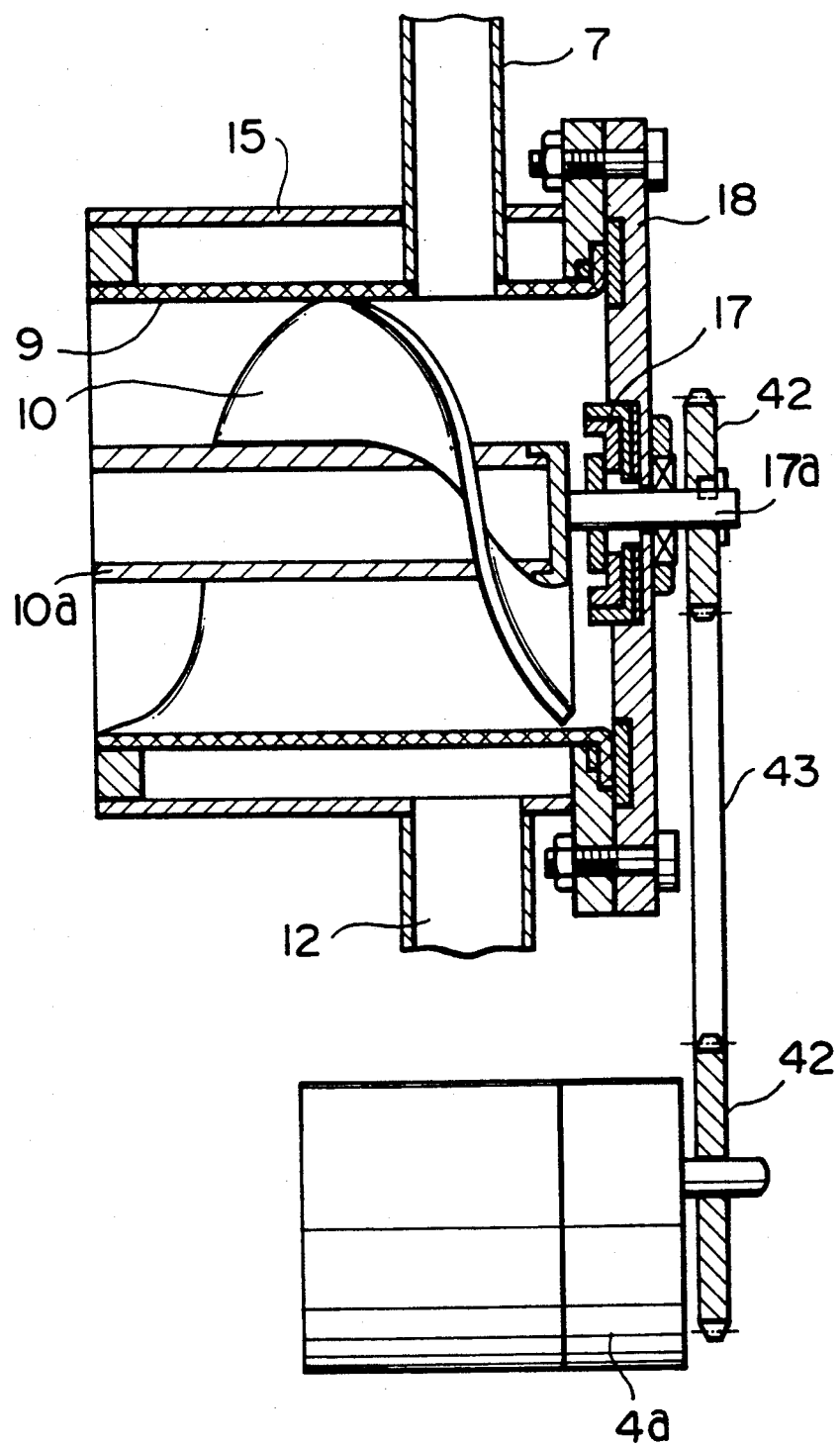
FIG. 7 is a fragmentary vertical sectional view which illustrate a system for mechanically and biologically decomposing garbage in accordance with another embodiment of the present invention.

FIG. 7 is a fragmentary sectional view which illustrates a system for mechanically and biologically decomposing garbage in accordance with another embodiment of the present invention. According to this embodiment, the piping 7 vertically extending along the garbage decomposing vessel 23 is arranged directly above the solid/liquid separator 4, while the motor 4a for driving the solid/liquid separator 4 is arranged directly below the solid/liquid separator 4. Arrangement of the piping 7 and the motor 4a in the above-described manner is intended to aid in the design and construction of the system of the present invention in smaller dimensions.

Referring to FIG. 7 again, a power transmission system using a pair of sprockets is employed for the system of the present invention and the motor 4a is firmly secured to an extension (not shown) from the flange-shaped wall 18.

Incidentally, the present invention should not be limited to the above-described power transmission system. Alternatively, a power transmission system using a pair of timing belt pulleys or gears may be substituted for the power transmission system employed for the system of the present invention.

Referring to FIG. 1 again, the system of the present invention is constructed such that the outer casing 21 of the garbage decomposing vessel 23 is watertightly mounted around the peripheral edge of a bottom plate 24 and a driving shaft 26 for rotationally driving the spiral stirring blade 30 is projected upward of the bottom plate 24 at its central position via a mechanical seal 25. One end of the driving shaft 26 is operatively connected to an universal joint 27 for the spiral stirring blade 30, while the other end of the same is operatively connected to a shaft 28 for the motor 5 for driving the spiral stirring blade 30.

The garbage decomposing vessel 23 is provided with a protective cover 29 at the bottom part thereof for the purpose of maintaining good lubrication but arrangement of the protective cover 29 is not always required, because the garbage decomposing vessel 23 is not used for stirring an inorganic material.

The lower end of a shaft 31 for the spiral stirring blade 30 is operatively connected to the universal joint 27, while the upper end of the same is operatively connected via an universal joint 33 to a shaft 32 for the motor 6 for turning the spiral stirring blade 30. A bearing 34 specially designed for turning movement of the spiral stirring blade 30 is attached to the ar plate 33 which in turn is fixedly secured to the shaft 32.

The motor shaft 32 and the arm plate 33 are designed such that they have a constant length, and the arm plate 33 turns in the region having a depth of 70 mm or more as measured from the upper surface of garbage decomposing bacillus growing bed 35. In addition, the spiral stirring blade 30 is arranged such that the solid disintegrated garbage which has been conveyed in the interior of the garbage decomposing vessel 23 by rotation of the spiral conveying blade 10 does not appear above the upper end of the garbage decomposing bacillus growing bed 35.

The purpose of holding the disintegrated garbage in the garbage decomposing bacillus growing bed 35 in the buried state is primarily in that reduction of a speed of biological decomposition of the disintegrated garbage is prevented, generation of a bad-smelling odor is minimized and a biological decomposing speed is made constant as far as possible throughout the garbage decomposing bacillus growing bed 35 while birth and growth of worms are reliably prevented. Therefore, the aforementioned purpose constitutes a significant feature of the present invention.

Next, operation of the system of the present invention will be described below.

An operator actuates a control board 36 for starting rotation of the disposer 3. At this time, in response to commands from the control board 36, the motor 4a for driving the solid/liquid separator 4 and the motor 5 for driving the stirring blade 30 are rotated. Subsequently, the motor 6 for turning the spiral stirring blade 30 is driven with a delay of several seconds. The purpose of driving the motor 6 with a certain period of delay in that way is that the load to be born by the motor 5 at the starting time can be reduced substantially.

As long as the disposer 3 is operated, the motor 5 and the motor 6 are driven in operative association with the disposer 3. Even though the disposer 3 has completed its operation, rotation of all the motors is not simultaneously stopped under control of the control board 36 but they are automatically stopped after a predetermined period of time elapses.

This is because a certain quantity of disintegrated garbage and water remain still in the piping 7 depending on the location where the disposer 3 is mounted and that complete discharging of the disintegrated garbage in the solid/liquid separating screen 9 should be accomplished while the spiral blade 10 in the solid/liquid separator 4 is rotated at a reduced speed for the purpose of assuring that separation of the disintegrated garbage from water is positively promoted.

As the disintegrated garbage is biologically decomposed in the garbage decomposing bacillus growing bed 35, water derived from the decomposed garbage in excess of a quantity of water required by the garbage decomposing bacillus growing bed 35 sinks through the garbage decomposing vessel 23 to reach the bottom plate 24 on which it is then collected. Thereafter, it is drained into a water storage tank 39 via an outlet port 37 and a piping 38.

According to the shown embodiment, normally, when two months elapse after decomposition of the garbage in the garbage decomposing bacillus growing bed 35 for several days, the garbage decomposing bacillus growing bed 35 becomes a reservoir for storing various kinds of useful fertilizer components derived from the biologically decomposed garbage. It has been found from the results obtained from a number of tests conducted on an experimental farm for several years that the foregoing fertilizer components are very effective especially for growing leaf vegetables (spinach or the like). Further, it has been found that when the daily generating biologically decomposed water is fed to potted plants every day as an organic liquid fertilizer, it exhibits a remarkable growing effect for the plants. Additionally, it was reported as an experimental example that a single potted kiwi seedling was grown with the organic liquid fertilizer only used therefor so that thirty six kiwi fruits were successfully grown.

According to the results derived from experiments conducted in the district westward of Kanto district, it has been found that the thermal insulating material 22 in the outer casing 21 is not required. On the other hand, it is recommended for the viewpoint of safety that the outer casing 21 is lined with a thermal insulating material 22 of hard polyurethane having a thickness of about 15 mm when the system of the present invention is employed in the very cold season in Tohoku district as well as Hokkaido district. It should be noted that it is not at all required that the outer casing 21 is additionally equipped with a heater on the inside or the outside thereof. This is because the garbage decomposing bacillus growing bed 35 itself serves as a thermal insulator and moreover it generates a heat by itself at all times with the result that the environmental temperature peripheral to the outer casing 31 is not adversely affected.

The kind of garbage to be decomposed varies from house to house depending on the living type or fashion of each house. However, it has been found from the results derived from a series of experiments that the system of the present invention assures that most foodstuff waste materials can be decomposed without any particular difficult or trouble.

One fact to be noted with respect to the system of the present invention is that not only an egg's shell, fish bones and a crab's carapace but also the head portion of a large salmon can completely be decomposed after one week such that their original shape can not visually be distinguished.

In view of the current status of promoting activities for protecting the natural environment from destruction on a global basis, one of problems from which each self-governing body in this country suffers is the problem of garbage disposal in the future. In this connection, it is believed that the current common sense of causing self-governing bodies to dispose of various kinds of garbage by themselves will disappear in the near future.

Economic growth and development lead to an increased intensity of purchasing power which in turn induces generation of various kinds of garbage at an increased rate as a meals eaten in each house are diversified year by year.

Generally, an expenditure required for disposing a garbage per one cubic meter amounts to several hundred hundred yens with a certain difference among self-governing bodies in this country in a case where the incinerating method is employed. It should be added that the foregoing expenditure may not include a depreciation amount to be counted for the incinerator.

As far as garbage derived from from each person in a house is concerned, the garbage should naturally be disposed by himself but not by a self-governing body, provided that it is obvious that the garbage can be disposed by each other. In practice, the present invention has been made based on the foregoing facts and provides a system for mechanically and biologically decomposing garbage with a minimized quantity of energy. As is apparent from the above description, the system of the present invention produces byproducts which can be used as a high quality of organic liquid fertilizer and powdered organic fertilizer. Therefore, the system of the present invention has a significant feature at the present time when a raw material required for producing any organic fertilizer is not practically available in this country.

Specifically, to operate the system of the present invention, electricity is required for rotating all the motors to biologically decompose garbage for several minutes at every time when the garbage is fed to the system. Therefore, a cost for the electricity can be reduced to a very low level under a normal condition that garbage to be disposed is fed to the system three times per day. In addition, a material for producing garbage decomposing bacillus growing bed in which disintegrated garbage is biologically disposed can very sanitarily be prepared such that pulverized wood (waste material derived from production of plate-shaped wood products) is thermally processed for the purpose of sterilization and gravel decomposing bacilli are then fed to the processed pulverized wood. It should be noted that no maintenance service is required during a continuous garbage decomposing operation which is performed with the garbage decomposing bacilli used therefor.

Since the garbage decomposing vessel is constructed in a very simple manner, this makes it possible to operate the system of the present invention with a small number of components within a short period of time. Additionally, such simple construction of the garbage decomposing vessel as described above makes it possible to reduce a manufacturing cost required for the system of the present invention to such a low level that it can easily be installed in an ordinary house. As will be apparent from the above description, the system of the present invention offers many advantageous effects with respect to not only saving of time, labor and spiritual load of a user but also environmental protection and economical load of each self-governing body and a national government.

As described above, the system of the present invention is substantially composed of a disposer, a solid/liquid separator and garbage decomposing vessel. With this construction, a large part of the water entering the solid/ liquid separator from the disposer is separated from the disintegrated garbage in the solid/liquid separator and then discharged to the outside via an outlet port. Thus, the solid disintegrated garbage only is introduced into the interior of the garbage decomposing vessel as the spiral conveying blade is rotated in the solid/liquid separator. As a result, a stirring operation can be performed in the garbage decomposing vessel at an improved operational efficiency.

While the present invention has been described above with respect to two preferred embodiments, it should of course be understood that the present invention should not be limited only to them but various changes or modifications may be made without departure from the scope of the invention as defined by the appended claims.

What is claimed is:

1. A system for mechanically and biologically decomposing a garbage, wherein said system comprises;
   a disposer for disintegrating said garbage in a large number of pieces,
   a solid/liquid separator arranged downstream of said disposer to receive the garbage which has been disintegrated by the disposer, said solid/liquid separator serving to separate water from the disintegrated garbage, and
   garbage decomposing vessel arranged downstream of said solid/liquid separator to receive the solid disintegrated garbage from the solid/liquid separator, said garbage decomposing vessel serving to biologically dissolve the solid disintegrated garbage from which water has been substantially separated in the solid/liquid separator.

2. A system for mechanically and biologically decomposing a garbage, said system including a disposer for disintegrating said garbage into a large number of pieces, a solid/liquid separator arranged downstream of said disposer to receive the garbage which has been disintegrated by the disposer, said solid/liquid separator serving to separate water from the disintegrated garbage and garbage decomposing vessel arranged downstream of said solid/liquid separator to receive the solid disintegrated garbage from the solid/liquid separator, said garbage decomposing vessel serving to biologically dissolve the solid disintegrated garbage from which water has been substantially separated in the solid/liquid separator, as claimed in claim 1, wherein
   (a) the disposer is arranged at an outlet port from the sink of a kitchen,
   (b) the upper end of a piping for allowing the garbage disintegrated by the disposer to be conveyed therethrough is connected to the disposer, while the opposite end of said piping is connected to an inlet port of the solid/liquid separator,
   (c) an outer casing of the solid/liquid separator is fixedly secured to an outer casing of the garbage decomposing vessel at a substantially middle location as seen in the direction of a depth of the garbage decomposing vessel, (d) a solid/liquid separating screen is accommodated in the solid/liquid separator with the aid of a water sealing ring and a packing ring serving as a bearing for said solid/liquid separating screen in the coaxial relationship relative to the solid/liquid separator, (e) a spiral conveying blade of which the outer peripheral surface comes in close contact with the inner wall surface of the solid/liquid separating screen is rotatably arranged in the solid/liquid separating screen to forcibly convey the disintegrated garbage in the garbage decomposing vessel, said spiral conveying blade including a shaft to which a shaft portion is connected so as to allow the solid/liquid separating screen to be driven by a motor, said shaft portion extending through a mechanical seal, (f) the outer casing of the garbage decomposing vessel is watertightly mounted on a bottom plate to which a mechanical seal is attached at the central part thereof so as to allow the shaft of a motor for rotating a spiral stirring blade via an universal joint to extend therethrough, said spiral stirring blade being adapted to rotate while turning in the garbage decomposing vessel, (g) the lower end of a shaft for the spiral stirring blade is operatively connected to said universal joint, while the upper end of the same is operatively connected to an arm plate for turning the spiral stirring blade in the garbage decomposing vessel, (h) said arm plate is fixedly secured to the shaft of a motor mounted above the arm plate to turn the spiral stirring blade in the garbage decomposing vessel, (i) said bottom plate for the outer casing of the garbage decomposing vessel is formed with an outlet port through which water produced by biological decomposition of the solid disintegrated garbage in the garbage decomposing vessel is drained in a reserving tank via a piping, (j) the inner wall surface of the garbage decomposing vessel is lined with a thermal insulating material, (k) the garbage decomposing vessel includes a decomposing bacillus growing bed of which upper surface is located to assume a level above the upper surface of the turning arm by a height of 80 mm and more, (l) a control board is arranged below the garbage decomposing vessel;

(i) said control board controls operation of a motor for rotating the spiral conveying blade in the solid/liquid separating screen, a motor for rotating the spiral stirring blade and a motor for turning the spiral stirring blade in operative association with an electricity supply source for the disposer such that only said motor for turning the spiral stirring blade starts rotation with a delay of five seconds from the time when other motors start rotation, (ii) all the motors continue to rotate for a certain period of time preset by a timer after the disposer is turned off, and they automatically stop rotation after the preset time elapses, and (iii) the motor for rotating the spiral stirring blade is automatically rotated for a preset period of time three times per day irrespective of whether the disposer is operated or not, and it automatically stops rotation after the preset time elapses; and (m) a diameter of the spiral stirring blade is dimensioned such that the spiral stirring blade is normally rotated in the vicinity of the inner wall surface of the garbage decomposing vessel while the shaft of the spiral stirring blade is held in the tilted state in the garbage decomposing vessel, the lower end part of the spiral stirring blade being normally located in the vicinity of the bottom wall of the garbage decomposing vessel.

3. A system for mechanically and biologically decomposing a garbage as claimed in claim 1, wherein the solid/liquid separator comprises a solid/liquid separating screen, an outer casing arranged outside of said solid/liquid separating screen, an outlet port through which water separated from the disintegrated garbage is drained, a spiral conveying blade adapted to be rotated while coming in close contact with the inner wall surface of the solid/liquid separating screen to forcibly convey the solid disintegrated garbage in the garbage decomposing vessel and a motor for rotating said spiral conveying blade.

4. A system for mechanically and biologically decomposing a garbage as claimed in claim 1, wherein the garbage decomposing vessel is equipped with a motor for rotating the spiral stirring blade and a motor for turning the spiral stirring blade in operative combination with each other.

* * * * *